United States Patent
Atiba

(10) Patent No.: US 10,350,226 B1
(45) Date of Patent: Jul. 16, 2019

(54) THERAPY AND PREVENTION OF PRION PROTEIN COMPLEX INFECTIONS

(71) Applicant: Joshua O. Atiba, Watsonville, CA (US)

(72) Inventor: Joshua O. Atiba, Watsonville, CA (US)

( * ) Notice: Subject to any disclaimer, the term of this patent is extended or adjusted under 35 U.S.C. 154(b) by 0 days.

(21) Appl. No.: 16/118,349

(22) Filed: Aug. 30, 2018

Related U.S. Application Data

(60) Provisional application No. 62/690,736, filed on Jun. 27, 2018, provisional application No. 62/691,910, filed on Jun. 29, 2018, provisional application No. 62/714,012, filed on Aug. 2, 2018.

(51) Int. Cl.

| | | |
|---|---|---|
| *A61K 31/65* | (2006.01) | |
| *A61P 37/06* | (2006.01) | |
| *A61P 31/04* | (2006.01) | |
| *A61K 31/436* | (2006.01) | |

(52) U.S. Cl.
CPC .............. *A61K 31/65* (2013.01); *A61P 31/04* (2018.01); *A61P 37/06* (2018.01); *A61K 31/436* (2013.01); *A61K 2300/00* (2013.01)

(58) Field of Classification Search
CPC ........ A61K 31/65; A61K 31/04; A61K 31/06; A61K 31/436
See application file for complete search history.

(56) References Cited

U.S. PATENT DOCUMENTS

| | | | |
|---|---|---|---|
| 9,453,079 B2 | 9/2016 | Atwal et al. | |
| 9,919,021 B2 | 3/2018 | Ferreira Vila Real et al. | |
| 9,999,624 B2 | 6/2018 | May et al. | |
| 2001/0014670 A1* | 8/2001 | Balin ...................... | A61K 31/00 514/29 |
| 2009/0209497 A1* | 8/2009 | Folkman ................ | A61K 31/65 514/154 |
| 2012/0064143 A1* | 3/2012 | Sharp ................... | A61K 9/1635 424/439 |
| 2015/0265582 A1* | 9/2015 | Armer ................ | A61K 31/4196 424/451 |
| 2017/0333469 A1* | 11/2017 | Vogt ..................... | A61K 9/0024 |

OTHER PUBLICATIONS

Budni, Josiane & Garcez, Michelle & de Medeiros, J & Cassaro, E & Santos-Bellettini, T & Mina, F & Quevedo, Joao. (2016). The Anti-Inflammatory Role of Minocycline in Alzheimer's Disease. Current Alzheimer research. Bentham Science Publishers, vol. 13, No. 12.
Baskakov et al. Converting the prion protein: What makes the protein infectious, Biochimica et Biophysica Acta (BBA)—Molecular Basis of Disease. vol. 1772, Issue 6, Jun. 2007, pp. 692-703.
Cheng, Shanshan et al. "Minocycline reduces neuroinflammation but does not ameliorate neuron loss in a mouse model of neurodegeneration." Scientific reports (2015).
UK Research and Innovation, Minocycline in Alzheimer's Disease Efficacy Trial: The MADE Trial, Journal. https://gtr.ukri.org/projects?ref=MC_PC_13091. Last accessed Aug. 17, 2018. Total of 4 pages.
Minocycline in Alzheimer's Disease. ISRCTN—ISRCTN06195297: Ongoing 2b/3a Inhibition in Myocardial Infarction Evaluation, www.isrctn.com/ISRCTN16105064. Last accessed Aug. 17, 2018. Total of 7 pages.
Minocycline in Patients With Alzheimer's Disease, NIH U.S. National Library of Medicine, ClinicalTrials.gov, https://clinicaltrials.gov/ct2/show/study/NCT01463384?sect=X4301256. Last accessed Aug. 17, 2018. Total of 16 pages.
Parry T.L., Melehani J.H., Ranek M.J., et al. (May 2015) Functional amyloid signaling via the inflammasome, necrosome, and signalosome: new therapeutic targets in heart failure. Frontiers in Cardiovascular Medicine, vol. 2, Article 25. Total of 14 pages.
Brendan M. Weiss, Sandy W. Wong, Raymond L Comenzo, Beyond the plasma cell: emerging therapies for immunoglobulin light chain amyloidosis, American Society of Hematology, Journal. Blood May 12, 2016, blood-2015-11-681650; DOI: 10.1182/blood-2015-11-681650. Last accessed Aug. 28, 2018. Total of 7 pages.
Zhou J, Liu B (2013) Alzheimer's disease and prion protein. Intractable & Rare Disease Research, Journal 2(2): pp. 35-44. https://doi.org/10.5582/irdr.2013.v2.2.35. Total of 10 pages.
Kaeberlein M, Galvan V., "Rapamycin and Alzheimer's disease: Time for a clinical trial?" Science Translational Medicine. Jan. 23, 2019. vol. 11, Issue 476, eaar4289. DOI: 10.1126/scitranslmed.aar4289.
Solis, Gregory M et al. "Translation attenuation by minocycline enhances longevity and proteostasis in old poststress-responsive organisms." eLife vol. 7 e40314. Nov. 27, 2018, doi:10_7554/eLife.40314.

* cited by examiner

*Primary Examiner* — Umamaheswari Ramachandran
(74) *Attorney, Agent, or Firm* — SoCal IP Law Group LLP; Steven C. Sereboff; Brian S. Tamsut

(57) ABSTRACT

There are disclosed therapies and preventions of prion protein complex infections. The transcription of the amyloid precursor protein gene and PrP gene and the RNA transcript are the rate-limiting steps and are most susceptible for blockage and control of the process of amyloid protein formation and PrP$^{sc}$ formation. Thus, therapies and prevention regimes for prion protein complex infections interrupt this process at the level of DNA transcription to RNA, RNA transport to the mitochondrion for protein synthesis and deposition in the cerebral cortex neurons.

1 Claim, 5 Drawing Sheets

The Witch's Brew

THERAPY AND PREVENTION OF PRION PROTEIN COMPLEX INFECTIONS

RELATED APPLICATION INFORMATION

This patent claims priority from the following provisional patent applications:

Application No. 62/690,736 filed Jun. 27, 2018 entitled "Treatment of Alzheimer's Disease;" Application No. 62/691,910 filed Jun. 29, 2018 entitled "Preventive Therapy of Alzheimer's Disease;" and Application No. 62/714,012 filed Aug. 2, 2018 entitled "Therapy and Prevention of Alzheimer's Disease."

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to therapy and prevention of prion protein complex infections.

Description of the Related Art

AD is commonly believed to be a localized brain disease. AD with neurological disease is the third leading cause of death in the United States after cardiovascular diseases and cancer. AD normally follows a sequence comprised of neuro-inflammation, amyloid and tau proteopathy, accumulative storage disease, neurotoxicity and neurodamage, loss of function (i.e., activities of daily living (ADL) and cognitive skills), and finally death. AD deaths are due to the futility and loss of will to live in these patients who have been depersonalized and lost the will to live, coupled with the failure to thrive leading to premature death usually within five to ten years of diagnosis of AD.

There are four main prevailing theories about the causation of AD: (a) a cholinergic hypothesis, (b) an amyloid protein deposition hypothesis, (c) a tau protein deposition hypothesis, and (d) a neurovascular hypothesis. Presently there is no effective treatment capable of modifying the progression of Alzheimer's disease, or preventing its onset. Currently available therapies only act on symptomatic improvement, while the development of therapies capable of blocking or delaying the disease progression remains a challenging unmet need.

According to the cholinergic hypothesis, degeneration of cholinergic neurons in the basal forebrain and the associated loss of cholinergic neurotransmission in the cerebral cortex and other areas contributed significantly to the deterioration in cognitive function seen in patients with Alzheimer's disease.

Under the amyloid protein deposition hypothesis, the formation of amyloid plaques and neurofibrillary tangles are thought to contribute to the degradation of the neurons (nerve cells) in the brain and the subsequent symptoms of Alzheimer's disease. Amyloid proteins are a large group of proteins of which sixty different types have been described. Thirty-six amyloid proteins have been associated with human disease. Amyloid protein was first seen and described by Rudolf Virchow who thought it was a starchy substance hence the name amyloid related to starch or "amylin" in Latin. It was next thought to be a fatty substance, but later found to be a protein substance. Since the introduction of elegant protein chemistry, mass spectrometry, and x-ray crystallography, amyloid proteins have been better characterized and classified in various human diseases and conditions.

Amyloid protein disease was once classified as primary or secondary. Primary disease was recognized as synthesis and deposition of the protein in organs such as the heart, kidney, skin, tongue etc. In secondary disease, amyloid protein deposition was recognized as secondary to a chronic suppurative condition such as tuberculosis or other uncontrolled bacterial abscess which is common in developing nations of the world. Similarly, chronic inflammatory conditions, such as rheumatoid arthritis and renal dialysis, lead to reactive amyloid protein deposition.

Amyloid precursor protein (APP), which is encoded in chromosome 21, has a role in AD. APP is a trans-membrane protein that penetrates through the neuron's membrane, and is critical for neuron growth, survival, and post-injury repair. Thus, loss of a neuron's APP may affect physiological deficits that contribute to dementia. Clinical data from individuals with Down syndrome (i.e., trisomy 21) shows that they develop AD earlier in their 40s, since the gene for APP is in chromosome 21, and they are saddled with three copies. This is akin to patients with inflammatory bowel disease (IBD) who develop colon cancer in their 30-40s compared to normal population who develop it in their 50s to 80s. APP is copied and used to synthesize amyloid protein.

Amyloid beta (Aß) is the specific amyloid protein implicated in AD. Amyloid plaques are made up of small peptides, 39-43 amino acids in length. Amyloid beta is produced from the sequential cleavage of APP by beta-site amyloid precursor protein-cleaving enzyme 1 (BACE-1) followed by gamma-secretase. In AD, gamma secretase and beta secretase act together in a proteolysis catabolic reaction, cleaving a smaller fragment of APP. These protein catabolism fragments then form fibrils of amyloid beta, which further form clumps deposited outside the neurons known as senile plaques.

Because Aβ accumulates excessively in AD, there is a logical inference that its precursor, APP, would be elevated as well. However, a study has shown that neuronal cell bodies contain less APP as a function of their proximity to amyloid plaques. It has been theorized that this APP deficit near Aß plaques results from a decline in production of APP which normally rises in response to stress.

Several BACE-1 inhibitors and humanized monoclonal antibodies to soluble amyloid protein have been in clinical trials in AD. These trials failed to deliver on the promise of being disease modifying drug (DMD) agents (i.e., they change the underlying pathology of the disease) in AD. Similarly, vaccines have been tried to clear amyloid protein plaques in AD all to no avail. In light of the failure of clinical trials using BACE inhibitors, and the failure of amyloid immunotherapy with intravenous Solanezumab, the amyloid protein deposition theory has been called into question.

The tau protein deposition hypothesis proposes that tau protein abnormalities initiate the disease cascade. In this model, hyperphosphorylated tau begins to pair with other threads of tau. Eventually, they form neurofibrillary tangles inside nerve cell bodies When this occurs, the microtubules disintegrate, destroying the structure of the cell's cytoskeleton which collapses the neuron's transport system. This may result first in malfunctions in biochemical communication between neurons and later in the death of the cells.

The neurovascular hypothesis claims that a substantial amount of Aß peptide in the brain of Alzheimer's disease patients is originated in the systemic circulation. According to this theory, poor functioning of the blood-brain barrier (BBB) is involved. One side effect of this poor function is production of amyloid and tau hyper-phosphorylation.

Prion (PrP) is a protein which arises from misfolding of a normal protein. The two forms of prion are designated as $PrP^c$, which is a normally folded protein, and $PrP^{sc}$, a misfolded form which gives rise to the disease. The two forms do not differ in their amino acid sequence, however the pathogenic $PrP^{sc}$ isoform differs from the normal $PrP^c$ form in its secondary and tertiary structure. The $PrP^{sc}$ isoform is more enriched in beta sheets, while the normal $PrP^c$ form is enriched in alpha helices. The differences in conformation allow $PrP^{sc}$ to aggregate and be extremely resistant to protein degradation by enzymes or by other chemical and physical means. The normal form, on the other hand, is susceptible to complete proteolysis and soluble in non-denaturing detergents. It has been suggested that pre-existing or acquired $PrP^{sc}$ can promote the conversion of $PrP^c$ into $PrP^{sc}$, which goes on to convert other $PrP^c$. This initiates a chain reaction that allows for its rapid propagation, resulting in the pathogenesis of prion diseases. $PrP^c$ protein is one of several cellular receptors of soluble amyloid beta (Aß) oligomers.

Against this background of prion protein complex infections, we turn to several drugs which have not been proposed for therapeutic application toward prion protein complex infections. For example, although genetically engineered antibodies have been tried, antibiotics have not been considered as possible therapies for prion protein complex infections. Another class not previously considered are immunosuppressants.

The tetracyclines are a very old group of bacteriostatic antibiotics consisting of tetracycline, doxycycline and minocycline. They act by inhibiting protein synthesis in bacterial and protozoa cells and in eukaryotic organism mitochondrion, inhibiting the binding of aminoacyl-tRNA to the mRNA ribosome complex. They do so mainly by binding to the 30S ribosomal subunit in the mRNA translation complex. In addition to inhibiting protein synthesis, these drugs are anti-inflammatory, are lipid soluble, and have high central nervous system concentration.

Sirolimus, also known as rapamycin, is a macrolide compound marketed under the trade name Rapamune by Pfizer. Sirolimus has immunosuppressant effects in humans and is used in preventing the rejection of kidney transplants. It inhibits activation of T cells and B cells by reducing their sensitivity to interleukin-2 (IL-2) through mTOR inhibition. By its effect on B cells it prevents the humoral immune system from synthesizing humoral antibodies to the renal graft.

DETAILED DESCRIPTION

AD is not a localized brain disease. Like other prion protein complex infections, AD is a systemic disease involving both the body and the peripheral circulation and B-cells. AD includes a localized reaction in the neocortex. Indeed, proof of this is the fact that AD can be diagnosed in saliva by testing for Ab42 level (with ELISA test), blood Ab42/40 ratio, and cerebrospinal Ab42 level.

Amyloid beta protein deposition seen in AD is secondary to a chronic neuro-inflammatory condition in the acetylcholine discharging neurons of the cerebral cortex. This amyloid protein deposition starts ten to fifteen years prior to the clinical diagnosis of AD in the patient and continues until the patient dies. The transcription of the APP gene and the RNA transcript are the rate-limiting steps and are most susceptible for blockage and control of the process of amyloid protein formation. Thus, there is described herein a cure for AD based upon interruption of this process at the level of DNA transcription to RNA, RNA transport to the mitochondrion for protein synthesis and deposition in the cerebral cortex neurons. This is the main thrust of our effort in introducing the first DMDs in AD.

This neuroinflammation in the neocortex is concomitant with localized secretion of amyloid beta to the acetylcholine secreting memory nerve fibers, and the secretion of cellular prion protein ($PrP^c$) peptides and tau protein peptides. Because of the neurotoxicity of the amyloid protein oligomers there is the misfolding of the $PrP^c$ peptides converting them from an alpha helical structure to a beta helical structure (i.e., $PrP^{sc}$). The $PrP^{sc}$ beta helical structure interacts with Aß fibrils and starts laying down sheets of Aß fibrils which are neurotoxic and lead to neurotoxicity and nerve fiber and nerve cell death creating the pathognomonic amyloid plaques and the tau protein tangles.

Figure 1:
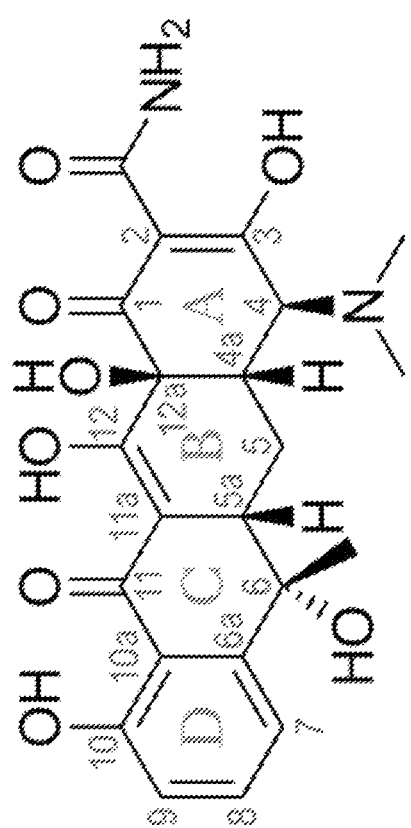
FIG. 1 is a skeletal formula of tetracycline with atoms and four rings numbered and labeled.
Figure 2:
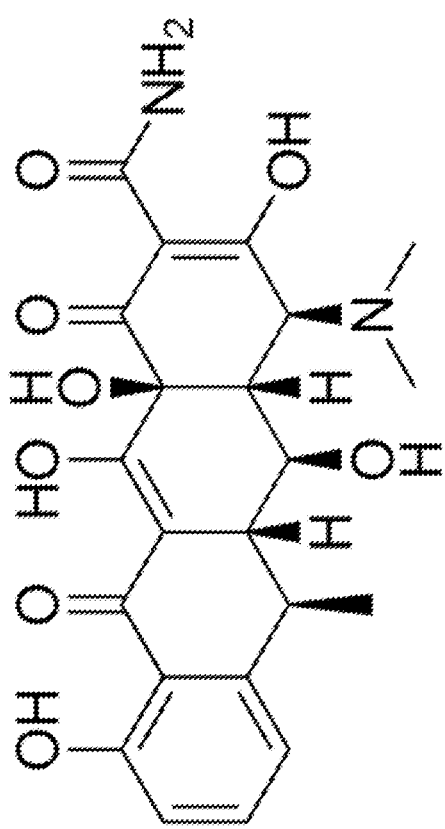
FIG. 2 is a formula for doxycycline.
Figure 3:
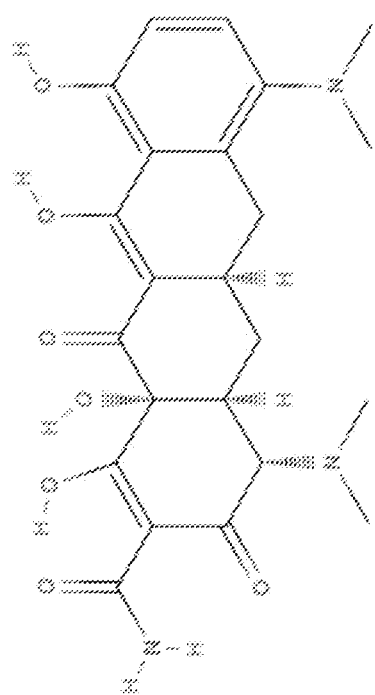
FIG. 3 is a formula for minocycline.
Figure 4:
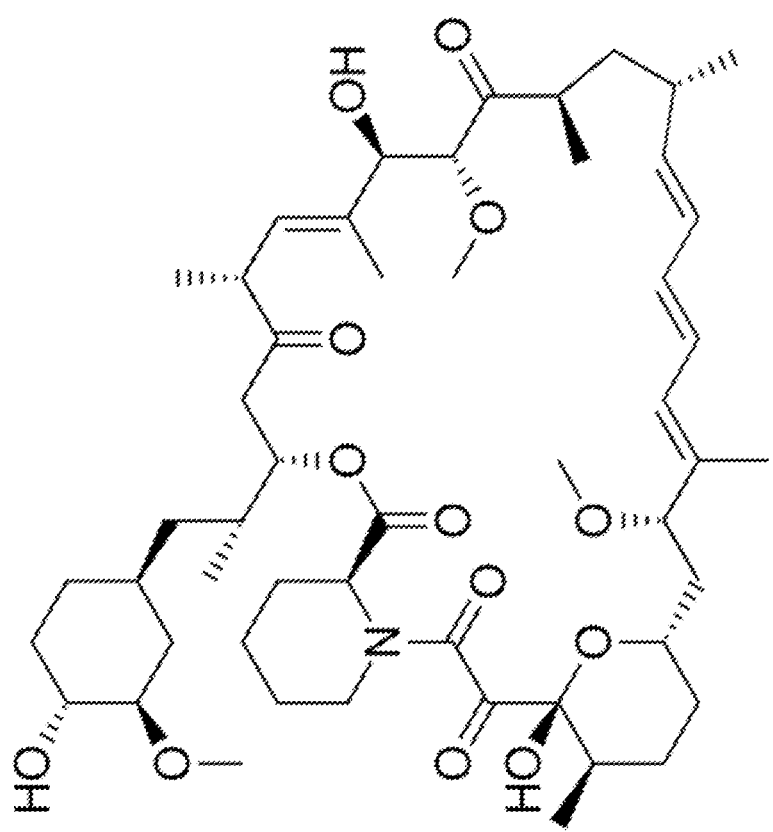
FIG. 4 is a formula for sirolimus.
Figure 5:
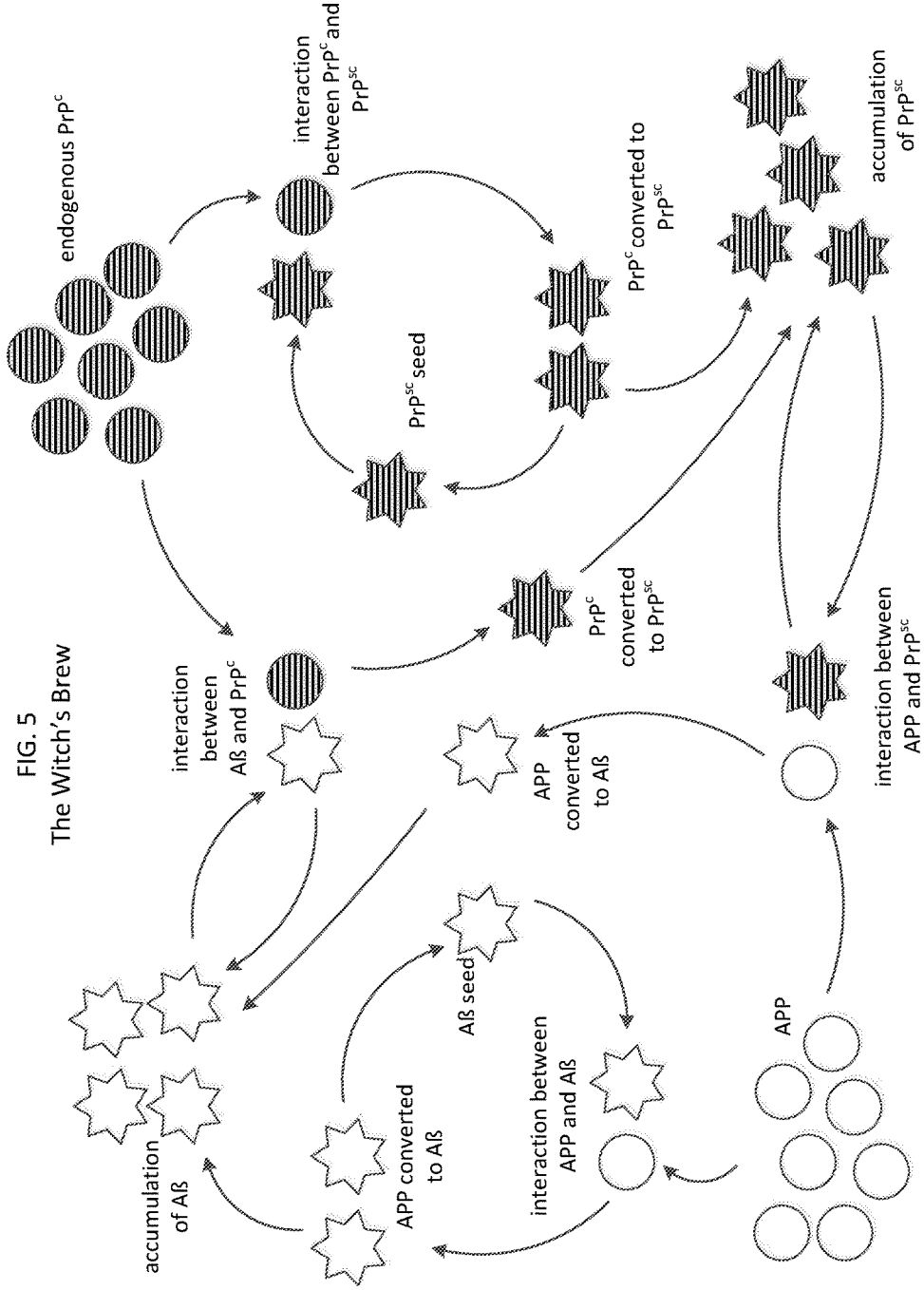
FIG. 5 is a conceptual diagram showing how the basis for exponential growth of the presence of Aß and $PrP^{sc}$.

The preventative and curative therapies described herein for prion protein complex infections have a dual interaction, and this dual interaction is necessary to halt the progress of the disease, undo at least some of its damage, and prevent it from re-arising or recurring. FIG. 5 demonstrates the basis for exponential growth of the presence of Aß and $PrP^{sc}$. As shown in FIG. 5, when $PrP^{sc}$ is applied to $PrP^c$, the $PrP^c$ misfolds into $PrP^{sc}$. The same behavior arises with APP and Aß: Aß is a seed for producing more Aß from APP. However, these two cycles are not independent. They are interdependent. That is, Aß seeds conversion of $PrP^c$ into $PrP^{sc}$, and $PrP^{sc}$ seeds production of Aß from APP. Thus, this witch's brew of Aß and $PrP^{sc}$ at the heart of prion protein complex infections is a cycle of death which cannot be stopped by a therapy which only interferes with misfolding of $PrP^c$ into $PrP^{sc}$, or only interferes with production of Aß from APP. The therapy described herein addresses both types of misfolding.

Prion protein complex infections may be treated and prevented through two treatment forms. In these infections, amyloid beta protein, present in the blood, diffuses into the cerebrospinal fluid which washes over the brain and the neocortex. This creates a secondary neocortical reaction with the laying of sheets and sheets of amyloid beta fibrils, leading to the death and destruction of memory cells and creating amyloid plaques and neurofibrillary tau protein tangles. One treatment form uses an immunosuppressant to address the systemic humoral B cell reaction and prion protein transcription, translation and synthesis. The other treatment form uses an antibiotic to address synthesis of amyloid beta protein. Benefits are obtained by combining the treatment forms.

Prion protein complex infections arise from a complex of rogue prion proteins—a "witches brew." This rogue prion protein complex consists of Aβ fibrils and prion protein beta ($PrP^{sc}$) fibrils. The body's natural reaction to the rogue prion protein complex is a self-defense mechanism that itself irreparably destroys tissue. These defense mechanisms take the form of a self-assembling Pacman which attacks and eats the rogue prion protein complex. Injury to the corresponding tissue is the culprit in the pathogenesis of AD and other prion protein complex infections.

The systemic disease component of prion protein complex infections may be treated with an immunosuppressant such as sirolimus. Sirolimus, by its effect on B cells, impairs the humoral immune system from synthesizing humoral antibodies and APP. This abrogates the systemic component of the AD pathogenesis.

The central nervous system (CNS) localized effects of prion protein complex infections may be treated with antibiotics such as tetracyclines. Tetracyclines block protein synthesis by their effects on transcription, translation, and binding to the ribosomal protein complexes. The tetracycline compounds can deal with the CNS/neocortical component of the AD pathogenesis by inhibiting the transcription of the APP gene on chromosome 21 and the transcription of the PrP gene on chromosome 20. Additionally, the tetracyclines block translation of the gene and protein synthesis by binding to the 30S and 50S subunits of the ribosomal protein complex.

The double action through treatment of both the systemic disease component and the CNS localized effects leads to hindering or abolition of the effect of the rogue prion protein complex. By inhibiting the transcription and blocking the synthesis of amyloid protein in AD patients, we stop further amyloid protein deposition in the cerebral cortex and the subsequent neurotoxicity and neuronal damage and loss of memory and function. Patients accordingly regain function and are able to participate in their activities of daily living and interactions with family members. Similarly, by blocking the transcription and synthesis of $PrP^{sc}$, the second part of the rogue prion protein complex is disrupted.

For patients with AD, the therapy may be either an antibiotic alone, or an antibiotic in combination with an immunosuppressant. For an adult, an appropriate therapy may be one of the following: (a) doxycycline 100 mg twice per day such as in the morning and in the evening; (b) a first dose of doxycycline 100 mg and sirolimus 2 mg taken together, such as in the morning, and a separate dose of doxycycline 100 mg at another time, such as in the evening; (c) minocycline 100 mg and sirolimus 2 mg taken at the same time such as in the morning; (d) a single dose of minocycline 100 mg, such as in the morning.

A dose may take the form on a unit dose. That is, a unit dose is a pill, a tablet or a capsule—one and only one.

Effectiveness of this therapy is apparent in three to twelve months. Once treatment is effective, the patient may discontinue the therapy under controlled observation for relapse and possible retreatment. For AD patients, effectiveness may be measured by the Alzheimer's Disease Assessment Scale-Cognitive (ADAS-Cog) subscale and the Alzheimer's Disease Cooperative Study-Activities of Daily Life (ADCS-ADL) scale. Both of these tests have been developed over many years, and it is expected that they will continue to be refined.

These therapies may be varied in a number of ways. First, other inhibitors of protein synthesis at the level of transcription, translation and protein assembly may be used. Second, the dosage levels may be different, with daily dosages of doxycycline as low as 40 mg, minocycline as low as 25 mg, and sirolimus as low as 0.5 mg. On the upper end the dosages may be as much as 400 mg (e.g., 200 mg twice per day) of doxycicline, 300 mg (e.g., 150 mg twice per day) of minocycline, and 4 mg (e.g., 2 mg twice per day) of sirolimus. The dosages specified above are for an average adult, and dosage may be correlated to body weight, with heavier patients receiving a larger dose and lighter patients receiving a smaller dose. Dosages need not be correlated to age. Dosages may be slow release.

How often the pill is taken may be varied, as may the time of day. Every other day may be sufficient for some patients, or three days on and two days off. These are examples of drug holidays. Dosage may be different day-to-day. Time of day for taking the medication may be selected based upon the patient having an empty stomach for better absorption.

For individuals with a first or second degree relative diagnosed with AD and a positive saliva amyloid beta 42 test of 40 pg/ml or greater by ELISA, the same regime prevents AD or effectively treats undiagnosed AD and may be used as a preventative therapy.

Other antibiotics which may be used that inhibit protein gene transcription, translation and synthesis.

Other immunosuppressants may be used that block B cell function and synthesis of amyloid beta and $PrP^{sc}$, such as are cyclosporin, tacrolimus and everolimus.

Despite the failure of BACE inhibitors in treating AD, the amyloid protein deposition hypothesis is valid. These studies failed because the inhibitors acted downstream in the metabolism of amyloid protein. The therapies described herein work at the level of DNA transcription to RNA and RNA transport to the mitochondrion for protein synthesis by binding to the 30S and 50S subunits of the RNA to block amyloid protein synthesis. Plus, normal cellular catabolism eliminates already deposited amyloid protein.

The therapies described above are also effective for other prion protein complex infections. These include Creutzfeldt Jakob disease (CJD), Lewy body disease, Parkinson's disease, amyotrophic lateral sclerosis (ALS), cerebral amyloid angiopathy, and Down's syndrome.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A pharmaceutical composition consisting of:
   an antibiotic or a pharmaceutically acceptable salt thereof, wherein the antibiotic comprises 50 mg of minocycline;
   an immunosuppressive or a pharmaceutically acceptable salt thereof, wherein the immunosuppressive comprises 1 mg of sirolimus; and
   one or more pharmaceutically acceptable carriers, diluents, or excipients.

* * * * *